United States Patent [19]

Schmiedl

[11] Patent Number: 5,157,266
[45] Date of Patent: Oct. 20, 1992

[54] METHOD AND DEVICE FOR TESTING TRANSPARENT SHEETS

[75] Inventor: Roland Schmiedl, Bielefeld, Fed. Rep. of Germany

[73] Assignee: Stora Feldmuehle Aktiengesellschaft, Düsseldorf, Fed. Rep. of Germany

[21] Appl. No.: 573,040
[22] PCT Filed: Feb. 28, 1989
[86] PCT No.: PCT/EP89/00192
§ 371 Date: Oct. 23, 1990
§ 102(e) Date: Oct. 23, 1990
[87] PCT Pub. No.: WO89/08247
PCT Pub. Date: Sep. 8, 1989

[30] Foreign Application Priority Data

Feb. 29, 1988 [DE] Fed. Rep. of Germany ....... 3806385

[51] Int. Cl.$^5$ ............................................. G01N 21/88
[52] U.S. Cl. ..................................... 250/572; 250/563; 356/431
[58] Field of Search ............... 250/562, 563, 571, 572; 356/237, 238, 239, 431

[56] References Cited

U.S. PATENT DOCUMENTS

| 4,005,926 | 2/1977 | Neale et al. | 356/444 |
| 4,013,367 | 3/1977 | Nagao et al. | 356/200 |
| 4,277,178 | 7/1981 | Cashing et al. | 356/431 |
| 4,306,808 | 12/1981 | Vander Neut | 356/239 |
| 4,367,047 | 1/1983 | Ikin | 356/431 |
| 4,431,309 | 2/1984 | Sick et al. | 356/431 |
| 4,455,086 | 6/1984 | West et al. | 356/239 |
| 4,460,273 | 7/1984 | Koizumi et al. | 356/239 |
| 4,634,281 | 1/1987 | Eikmeyer | 356/431 |

FOREIGN PATENT DOCUMENTS

| 1219933 | 7/1982 | Canada . |
| 1573496 | 4/1970 | Fed. Rep. of Germany . |
| 2362935 | 7/1974 | Fed. Rep. of Germany . |
| 2411407 | 9/1975 | Fed. Rep. of Germany . |
| 2925734 | 1/1981 | Fed. Rep. of Germany . |
| 3129808 | 2/1983 | Fed. Rep. of Germany . |
| 3208042 | 10/1983 | Fed. Rep. of Germany . |
| 3223215 | 12/1983 | Fed. Rep. of Germany . |
| 3534019 | 2/1987 | Fed. Rep. of Germany . |
| 1507548 | 4/1978 | United Kingdom . |

Primary Examiner—David C. Nelms
Assistant Examiner—John R. Lee
Attorney, Agent, or Firm—Felfe & Lynch

[57] ABSTRACT

Method and device for inspecting transparent webs for the presence of defects which include scanning the web to be tested with a flying spot, directing the light passing through the web to a receiver system which has transparent and opaque regions, supplying pulses by a photoelectric transducer disposed in the receiver to a computer corresponding to the light intensity received at the receiver system, directing the light spot such that when the material web is free of defects the light spot covers the opaque and the transparent regions of the receiver system in a continuous alternation, supplying the light spot intensity changes representing the change of regions to the computer as pulses and the light intensity fluctuations based on defects to the computer as pulses, and in the computer evaluating these pulses while these pulses are separated according to the regions of the receiver system.

5 Claims, 5 Drawing Sheets

METHOD AND DEVICE FOR TESTING TRANSPARENT SHEETS

BACKGROUND OF THE INVENTION

The invention relates to a method and a device for inspecting transparent sheets or webs for the presence of defects, particularly enclosed core seeds, where the web to be tested is scanned by a flying light spot. The light passing through the web is directed onto a diffuser plate which has transparent and opaque regions and behind which a receiver is disposed. The photoelectric transducer disposed in the receiver feeds pulses which correspond to the intensity of the light impinging on the diffuser plate to a computer.

Transparent webs in accordance with the present invention are continuously manufactured webs made of a transparent plastic material or glass. Since the formation of core seeds is a problem that occurs particularly with float glass lines, the invention is explained with reference to the inspection of float glass webs. It is, however, not limited thereto.

Inspection devices for glass webs are known from DE-OS 31 29 808 and DE-OS 32 23 215. It is common to both publications that the material web to be tested is scanned with a flying light spot and that light which is deflected into the glass by a core seed is detected at the edge of the material and evaluated. If the core seed is located in the center of the material to be tested, the distance to be covered by the light across the glass is very long, and the absorption is consequently very high. Particularly during the inspection of slightly colored glass, this absorption can be so high that no evaluable light signals can be received at the edge of the web. Another disadvantage of this known device is that the receiver at the edge of the material web must be relatively well insulated against incident foreign light in order to detect and evaluate, via the photoelectric transducer, the minor intensities of the light deflected at the core seeds. Moreover, deformation occurring at the margin and deflecting the light must be taken into account which requires additional devices to collect the light.

It is another disadvantage that the width must be continuously monitored in order to avoid damages of the laterally disposed receivers.

It is an object of the present invention to improve these known devices such that even more intensely colored glass or glass webs of a large width can be properly inspected for core seeds.

In accordance with the invention, this object is achieved with a method for inspecting transparent webs for the presence of defects, particularly enclosed core seeds. The transparent web to be tested is scanned with a flying light spot and the light passing through the web is directed onto a receiver system which has transparent and opaque areas and behind which a receiver is disposed. The photoelectric transducer disposed inside the receiver feeds pulses to a computer which correspond to the light intensities incident to the receiver system. The accomplishment is characterized in that the light spot is directed such that when the material web is free of defects, it covers the opaque and the transparent area of the receiver system in a continuous alternation, the change of area and the deviations of the light intensities caused by defects are supplied to the computer as pulses. These pulses are then evaluated while separated according to the areas of the receiver system.

The problems that occur during the inspection of glass webs are such that a great number of different defects can occur, however, in addition to these error signals, it is also possible that like signals occur which may be due to a contamination of the surface of the glass web and hence also lead to error messages, so-called false defects. Different inspection methods were developed corresponding to the different ways of inspecting. A distinction is made between measurements in reflection and transmission. They can further be divided in the so-called mirror reflection, hence inspection in the bright field, hereinafter referred to as R/S measurement. Further, the so-called diffuse reflection, hence the inspection in the dark field, referred to as R/DF. Moreover, there is direct transmission, also a measurement in the bright field, referred to as T/D. The is direct transmission in the close dark field, referred to as T/DA and diffuse transmission in the dark field, referred to as T/DF.

In R/S the directly reflected light is detected via a photoelectric transducer. Light fluctuations then occur when a non-reflecting defect or an impurity does not allow the total amount of light to be reflected. In R/DF, the receiver is disposed such that only diffusely reflected light can be received. The receiver is in both cases disposed above glass web to be inspected.

Other possibilities of inspecting transmission include a receiver which is disposed underneath the glass web to be tested. When measuring in direct transmission T/D, the light beam which has passed the glass web enters a light-open gap and is deflected out of this gap—and possibly darkened by impurities. The deflection by defects and the darkening by impurities prevents the light beam from entering the receiver as a complete beam and the occurring light intensity is reduced and, hence, the photoelectric transducer triggers a pulse. When measuring in the close dark field T/DA, the light beam also passed through the glass web to be inspected. However, in case there are no defects, it does not reach the receiver but is blocked by an opaque layer, the so called stopper, which is applied onto the receiver disk. Only if the beam is deflected by a defect, it can enter the receiver at the right or left side of the stopper and then generate a pulse signal in the photoelectric transducer. In an inspection according to T/DF, the one or several receivers are disposed outside the direct beam passage such that only diffuse light enters the one or several receivers if the light beam encounters a defect while scanning.

Depending on the inspection method selected, external influences may have a more or less negative effect. The deposition of dirt, for example, on or under the glass web to be tested greatly affects the bright field, i.e. the evaluation during the inspection according to R/S and T/D is greatly impaired. During the inspection in T/DA, however, the evaluation is significantly less affected.

The R/S method hence permits detecting major deformation defects in the material web and identifying reflecting defects. However, it is not possible to detect small defects from small deformations or to spot core seeds.

Method T/DA permits both the detection of coarse surface deformations and surface deformations that are small in dimension. However, it is not possible to recognize small core seeds nor to identify reflecting defects.

Another false defect is caused by so called plating which refers to the vertical and twisting movement of the moving glass web. This also greatly impairs mirror reflection inspection, hence R/S.

Method T/D permits recognizing coarse deformations and detecting core seeds. It is, however, not suitable for the identification of reflecting defects. The detection of small defects with deformations is not as sensitive as in T/DA. Prior art hence offered possibilities of successively arranging several inspection stations in order to achieve a complete inspection of a glass web. This, however, calls for the installation of three complex aggregates, one behind the other which is not possible due to the limited space in the production lines. Moreover, high costs also oppose this.

SUMMARY OF THE INVENTION

With the proposal according to the invention, however, it is now possible to make use of only one single inspection system which allows evaluating all occurring mistakes without requiring additional space or incurring significant additional costs.

The device for inspecting transparent webs for the presence of defects, particularly core seeds, essentially includes a transmitter to generate a light beam, a traversing device for the light beam, a receiver with a diffuser plate for the transparent web to be inspected, and a computer to evaluate the pulses received by the receiver. The device is characterized in that the diffuser plate has transparent and opaque regions, and the traversing device has a rotating mirror polygon the surfaces of which are half blackened, and the transmitter sends out two light beams running parallel to one another.

During inspection, two light beams are directed onto the mirror polygon and impinge on a surface. However, only one beam impinges on a half which has a reflecting coating whereas the other beam impinges on a half which is blackened. The result is that only one light beam is directed over the material web and the other is absorbed by the blackened surface and hence not reflected. The beams scanning the material web change with another rotation of the mirror polygon since they impinge on a new surface where the black half is replaced by the half with a reflecting coating. This time the second beam is directed over the material web to be tested. It impinges, however, at a slightly different location, referred to the receiver. This means that when the first scanning beam was directed such that after it had passed across the material web to be tested, it impinged on the stopper which is the blackened center portion of the receiver, the second beam is directed such that it reaches the gap running between the stopper and the blackened marginal area. In the first case T/DA is applied and in the second case T/D.

If the material web to be tested contains a seed which had not caused a deformation in one of the two surfaces, hence a so called core seed, the latter, as opposed to glass defects with surface deformation, will cause, due to its symmetry, a substantially smaller deflection of the light beam. The seed acts as a lens of an extremely short focal distance. In the distant field—this is the receiver—it appears as a mere silhouette which, however, does not noticeably affect the straight forward course of the light beam. There is no light entering the transparent regions to the left or right side of the stopper. However, the subsequently following scanning beam that is directed onto the web operates according to the T/D measuring system. In this arrangement, the area of impingement of the scanning light spot is transparent within a small scanning gap area. To the right and left sides, however, a cover—the stopper and/or the marginal area—prevents the light from entering. Here, the defects are detected by a change in the light intensity that is received, i.e. a reduction of the incident light. This reduction in light intensity may be caused by a complete or partial deflection of the light beam out of the light-transparent area due to glass defects with a strong surface deformation, by a blocking of the light beam caused by core seeds and by opaque objects in the light beam such as impurities or tin deposits. In order to achieve this sensitivity, the glass is usually washed prior to defect detection so as to avoid these false defects.

In the measuring arrangement T/D, the background signal $I_0$ of the receiver is relatively great due to the constant incident light radiation. The intensity changes $\Delta I$ have to be correspondingly large in order to detect the ratio of $\Delta I$ to $I_0$ and to have a proper evaluation.

A consequence thereof is that in this measuring arrangement, the smallest detectable glass defects must still be slightly greater than in the measuring arrangement T/DA which are sensitive to glass defects with a surface deformation.

In the measuring arrangement T/DA, the background signal is very small since there is usually no incident light. Light reaches the photoelectric transducer only when defects cause parts of the light beam to be directed in the transparent regions of the diffusor to the left and the right of the shielded center covering, the stopper that is. Then a pulse is prompted. Since there is practically no light reaching the receiver when the material web is free of defects, the background signal $I_0$ is extremely small. This is already sufficient to detect very small amounts of light $\Delta I$ since the quotient of $\Delta I$ divided by $I_0$ is consequently great.

The two measuring arrangements can hence be mutually evaluated in the same computer and the defects can thus be optimally detected and evaluated. An evaluation is possible in that the receiver system operates in T/DA as long as a scan runs along the stopper in a defined manner. Glass defects cause the light to change from the non-transparent to the transparent range, hence the light scattering area. As long as a scan runs in a defined manner on one of the two permeable transparent areas, hence the gaps, the receiver system operates in the T/D arrangement. Light deflected out of the transparent scattered area of the gap by glass defects, either impinges on the stopper and/or the marginal area or is absorbed by the defects themselves.

The transmitter used for scanning may include two radiators, for example, lasers. In accordance with a preferred embodiment, however, only one laser is used, possibly a higher powered laser, with a beam splitter disposed downstream. The splitter, for example, can be a semitransparent mirror.

In accordance with a preferred embodiment of the invention, the mirror polygon has an even number of surfaces. During rotation, a blackened half is followed by a half with a reflecting coating.

Advantageously, the diffuser plate is provided with an opaque region and a transparent region extending to the left and/or the right thereof and covers the entire length of the disk.

BRIEF DESCRIPTION OF THE DRAWINGS

The subsequent drawings explain the invention.

a) a small deformation on the surface
b) a core seed
c) an impurity on the surface, FIG. 4 a diffuser for transmitted light.

DESCRIPTION OF A PREFERRED EMBODIMENT

Figure 1:
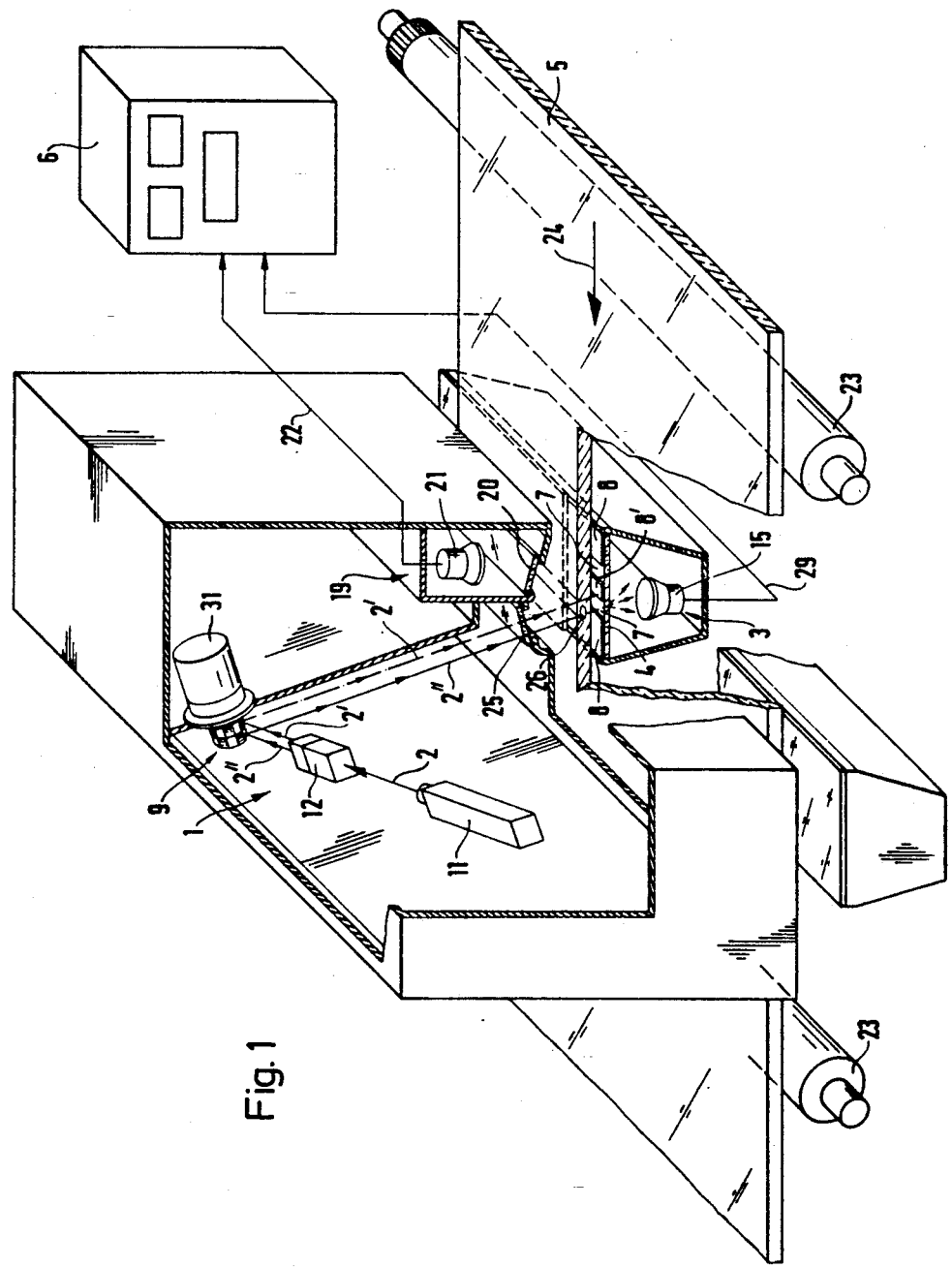
FIG. 1 is a perspective representation of the inspection device for transparent goods.
Figure 5:
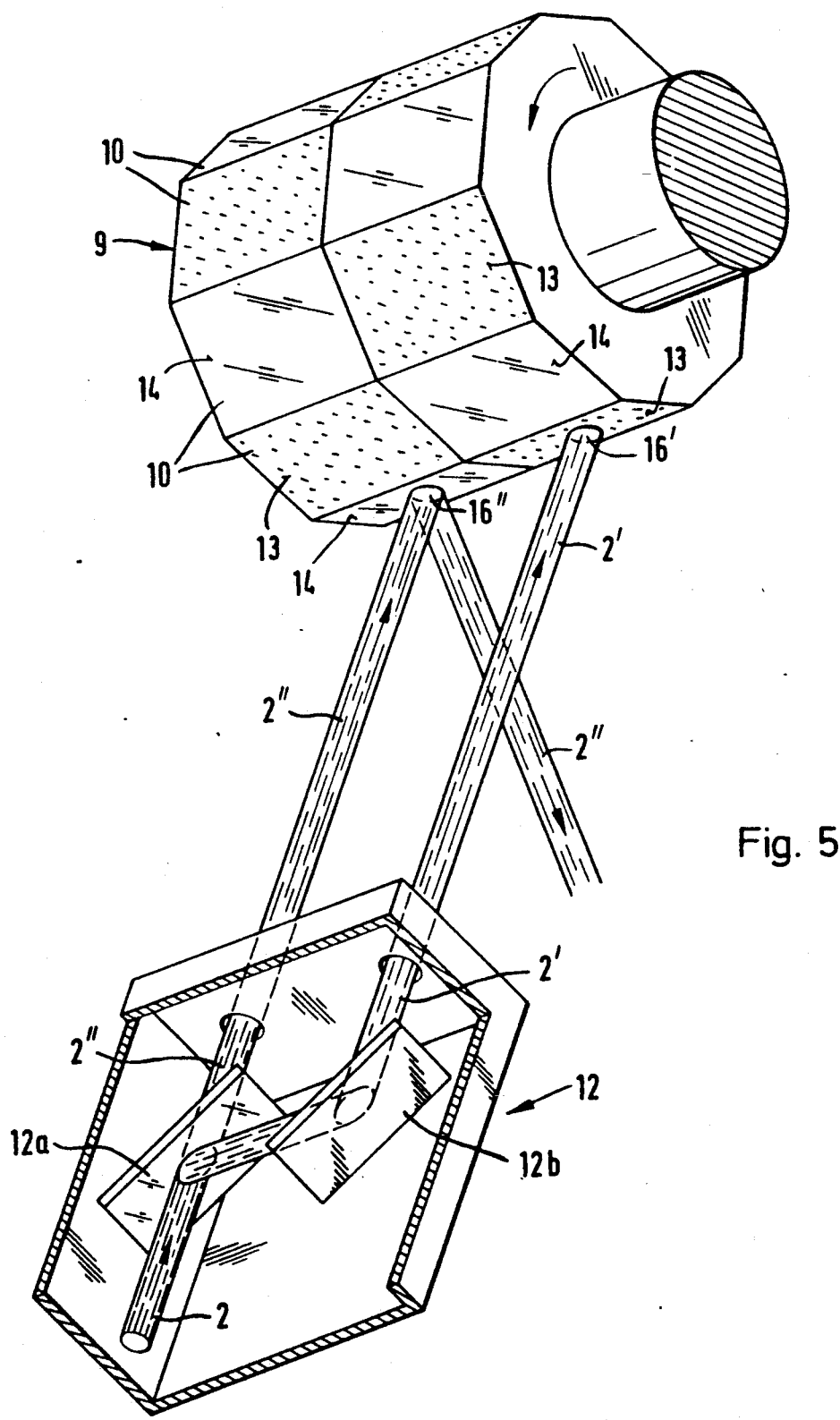
FIG. 5 shows the rotating mirror disk and diagrammatically disposed beam splitter.

The transmitter 1 includes the laser 11 and, disposed downstream thereof, the beam splitter 12 splitting the light beam 2 in the partial beams 2' and 2''. The beam splitter 12 comprises a semitransparent mirror 12a with a second mirror 12b associated thereto. The latter aligns the split partial beam 2' such that it is parallel to the partial beam 2'' and projects it onto the mirror polygon 9. These partial beams 2' and 2'' are directed onto the surfaces 10 of the mirror polygon 9 where they generate the light spot 16' and 16''. The partial beam 2' impinges on the blackened half 13 of a surface 10 and forms a light spot 16'. The partial beam 2'' impinges on the half 14 of the surface 10 which has a reflecting coating and here, it forms the light spot 16''. Whereas the light spot 16' is absorbed by the blackened half 13, the light spot 16'' is reflected, travels through the rotation of the mirror polygon 9 and serves to carry out measurements in direct transmission T/D (FIGS. 1, 5). It covers the entire width of the material web while forming a scanning line 27''.

Figure 2:
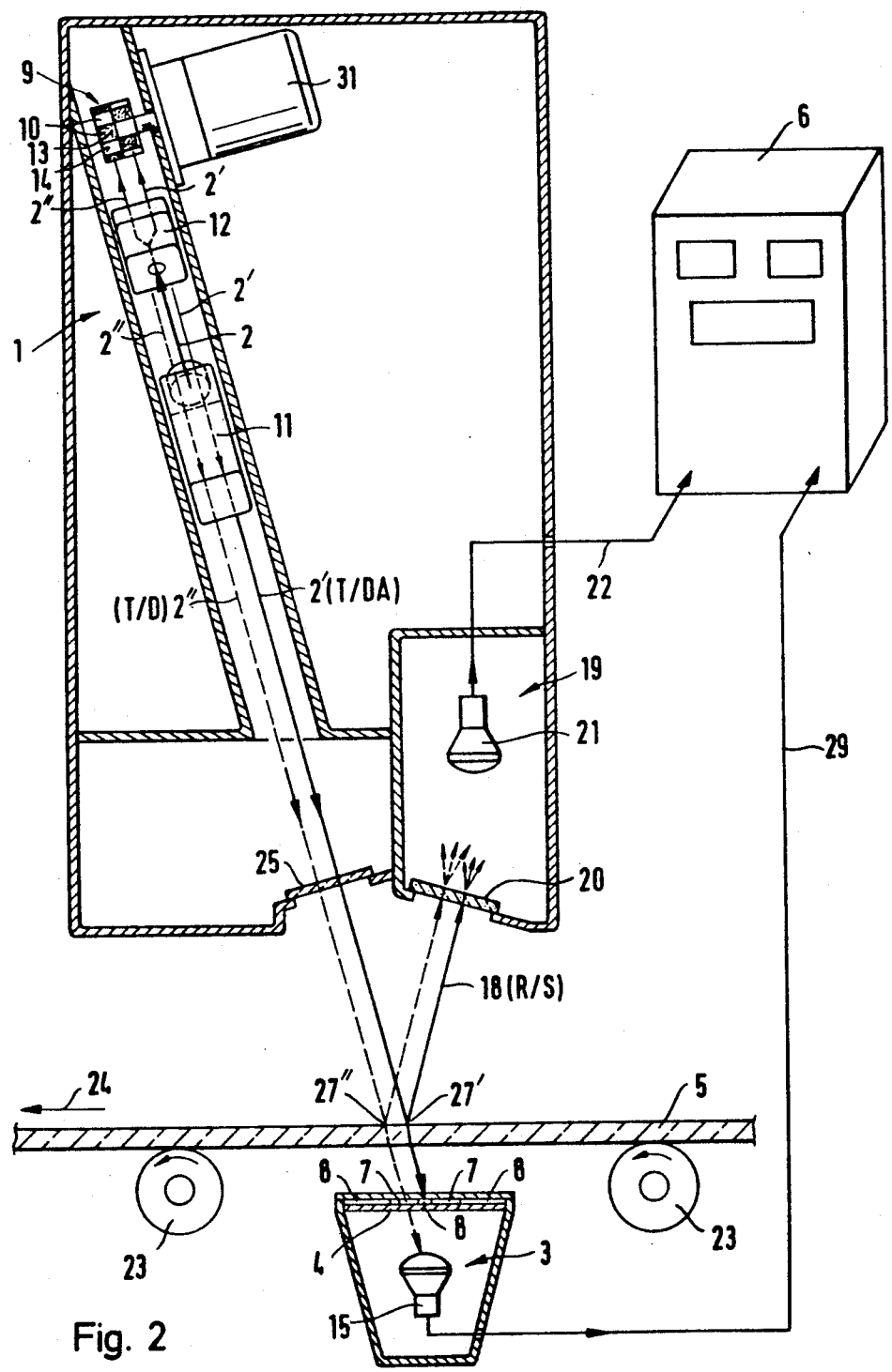
FIG. 2 is a lateral sectional view of the transmitter and the receiver of the inspection device.

After the drive motor 31 has rotated the mirror polygon 9 one more time by an angle determined by the number of facettes, the partial beam 2' impinges on the half 14 of the surface 10 which has a reflective coating and the partial beam 2'' impinges on the blackened half 13 of the surface 10, (FIG. 2). The material web 5 is thus scanned parallel to the first scanning, displaced by the distance of the partial beams 2', 2''. However, this scanning line 27' runs above the stopper 8' and the partial beam 2' hence falls on the opaque region 8' of the diffusor disk 4 provided there is no defect in the material web 5. During this scanning cycle, the computer 6 is switched to measuring in T/DA—during the previous cycle, it was switched to measuring in T/D—and it receives a pulse only when light enters the receiver 3 which was deflected by a defect in the material web. This alternating of measuring in T/D and T/DA is carried out while defined in a constant alternation and corresponding to the rotational speed and the numbers of facettes of the mirror polygon 9.

Figure 4:
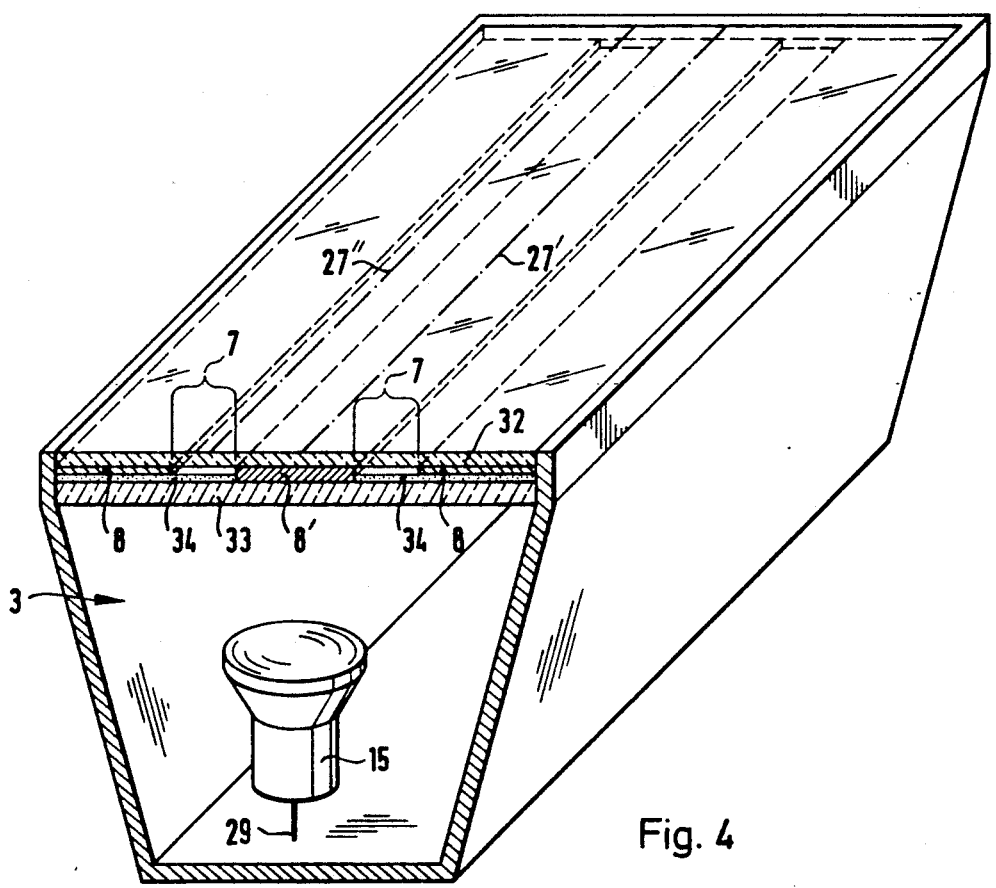

FIG. 4 shows the structure of the receiver 3 which, in a housing, contains the photoelectric transducers 15. The housing is covered by the a support cover 33 on which rests the diffusor disk 34. An opaque edge 8 is on top of the latter which is also separated by a centrally disposed stopper 8'. This stopper 8' is also made of an opaque material. This arrangement produces a transparent region 7 to the left and right of the stopper 8'. Across this region 7, the partial beams 2' and 2'' can enter the receiver 3. For further protection, the receiver 3 is covered by a covering disk 32.

FIGS. 1 and 2 show an embodiment where an additional mirror reflection receiver 19 is disposed above the material web 5. The mirror reflection receiver 19 is in the same housing as the transmitter 1 which sends its partial beams 2' and 2'' through the glass covering 25 in the lower part of the housing onto the material web 5. If only reflection measuring R/S is used, only one of the two partial beams, i.e. either partial beam 2' or partial beam 2'', is used. During the projection of the other beam, there is no evaluation of the reflected light signal. If the partial beam 2' impinges on the reflecting defect 17 (FIG. 3c), the latter projects the beam as a reflection beam 18 on the frosted glass pane 20 which is upstream of the mirror reflection receiver 19. Behind this glass pane, there is a photomultiplier 21 which converts the received light value into a pulse and supplies it over the pulse line 22 to the computer 6, (FIGS. 1 and 2). The subsequently occurring strong difference in brightness exhibits a pronounced difference to the light usually reflected by the material web 5, i.e. the light intensity is substantially higher.

Figure 3C:
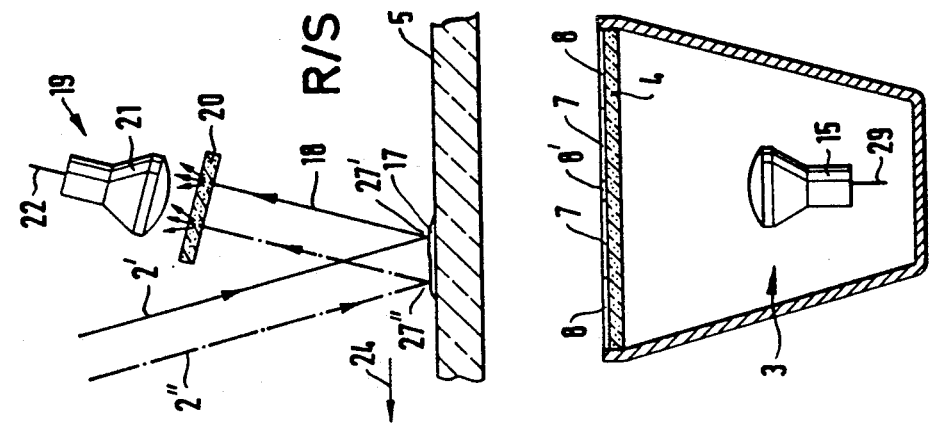
FIGS. 3a to 3c are diagrammatic representations of the beam characteristics in case of typical glass defects, these are.
Figure 3B:
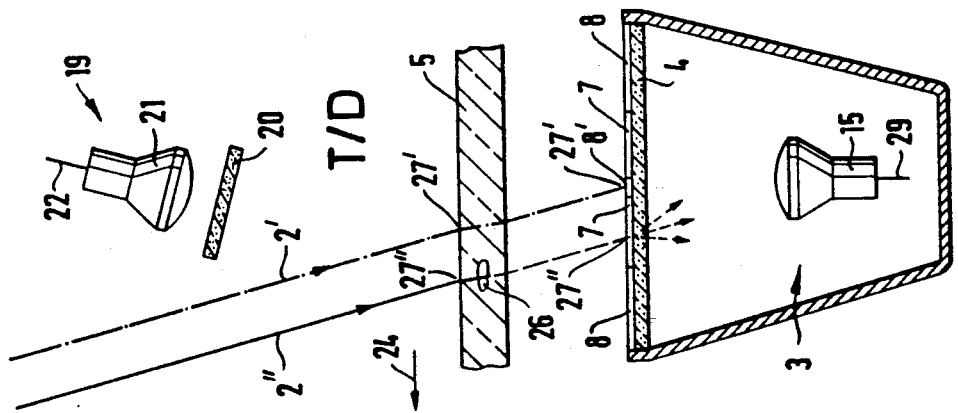
Figure 3A:
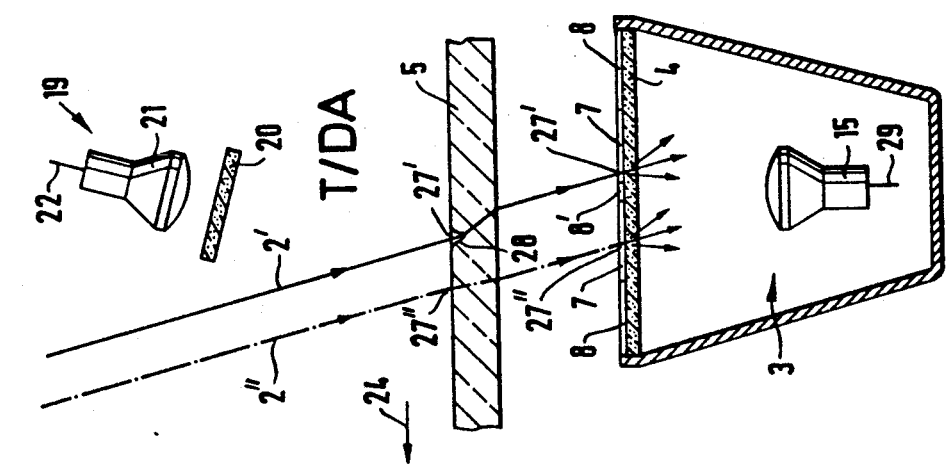

The characteristics of the beams for different defects is outlined in FIGS. 3a to 3c. In 3a, the measuring is carried out in T/DA, in 3b in T/D and in 3c in R/S. FIG. 3a shows a surface deformation 28 by which the partial beam 2' is deflected so that it does not impinge on the stopper 8' but instead it reaches the photoelectric transducer 15 through the transparent area 7. In FIG. 3c, the partial beam 2'' is analogously deflected by the core seed whereas both the partial beam 2' and the partial beam 2'' are projected through the pane 20 of frosted glass to the photomultiplier 21.

In the drawings, the material web is represented as a float glass web which is guided on rollers 23. It moves in direction of arrow 24 whereby the core seed 26 thus enters the region of the scanning lines 27', 27''. For a measuring in the close dark field T/DA, the light-deflecting properties, particularly of small core seeds 26, are very small so that its "obstructing effect" in the light beam (FIG. 3b) produces an intensity change only in the next scanning cycle, hence during the measuring in T/D. The transparent regions 7 are between stopper regions 8, 8'. The photoelectric transducer 15 in the receiver 3 converts this change in a pulse, and then supplies it via signal line 29 to the computer 6.

I claim:

1. Method of inspecting transparent webs for the presence of defects, particularly for enclosed core seeds, comprising: scanning the web to be tested with a flying light spot, directing the light passing through the web to a receiver system which has transparent and opaque regions, and supplying pulses by a photoelectric transducer disposed in the receiver to a computer corresponding to the light intensity received at the receiver system, directing the light spot such that when the material web is free of defects, the light spot covers opaque and the transparent regions of the receiver system in a continuous alternation, supplying light spot intensity changes representing the change of regions to the computer as pulses and the light intensity fluctuations based on defects to the computer as pulses, and in the computer evaluating these pulses while these pulses are separated according to the regions of the receiver system.

2. Device for inspecting transparent webs comprising: a transmitter for the generation of a light beam, a traversing device for the light beam, a receiver with a diffuser plate for light allowed to pass by a transparent material web to be tested and a computer for the evaluation of the pulses received by the receiver, the diffuser plate 4 having transparent 7 and opaque 8, 8' regions, the traversing device having a rotating mirror polygon 9 having surfaces 10 which are half blackened, the transmitter 1 sending out two light beams 2', 2" and both light beams 2, 2" running parallel to each other, the light beams 2, 2' being alternately transmitted to the receiver by the rotating mirror polygon 9.

3. Device in accordance with claim 2, in which the mirror polygon 9 has an even number of surfaces 10 and during the rotation of the mirror polygon 9, a blackened half 13 of the surfaces 10 follows a half 14 with a reflective coating.

4. Device in accordance with claim 2, in which the transmitter 1 comprises a laser 11 with a downstream beam splitter 12.

5. Device in accordance with claim 2, in which the diffuser plate 4 has an opaque region 8' extending over the entire length and at least one transparent region 7 on at least one of the left and right thereof.

* * * * *